(12) United States Patent
Rizzi

(10) Patent No.: US 9,850,217 B2
(45) Date of Patent: Dec. 26, 2017

(54) HIGH-PRESSURE REACTOR FOR THE SYNTHESIS OF MELAMINE

(71) Applicant: Casale SA, Lugano (CH)

(72) Inventor: Enrico Rizzi, Casnate con Bernate (IT)

(73) Assignee: Casale SA (CH)

( * ) Notice: Subject to any disclaimer, the term of this patent is extended or adjusted under 35 U.S.C. 154(b) by 0 days.

(21) Appl. No.: 15/123,924

(22) PCT Filed: Mar. 9, 2015

(86) PCT No.: PCT/EP2015/054807
§ 371 (c)(1),
(2) Date: Sep. 6, 2016

(87) PCT Pub. No.: WO2015/135868
PCT Pub. Date: Sep. 17, 2015

(65) Prior Publication Data
US 2017/0015636 A1    Jan. 19, 2017

(30) Foreign Application Priority Data

Mar. 12, 2014 (EP) ..................... 14159283

(51) Int. Cl.

| | |
|---|---|
| *C07D 251/60* | (2006.01) |
| *C07D 251/62* | (2006.01) |
| *B01J 19/24* | (2006.01) |
| *B01J 3/04* | (2006.01) |
| *B01J 10/00* | (2006.01) |
| *B01J 4/00* | (2006.01) |
| *B01J 3/02* | (2006.01) |

(52) U.S. Cl.
CPC .............. *C07D 251/60* (2013.01); *B01J 3/02* (2013.01); *B01J 3/04* (2013.01); *B01J 3/042* (2013.01); *B01J 4/002* (2013.01); *B01J 10/005* (2013.01); *B01J 19/246* (2013.01); *B01J 2219/00078* (2013.01); *B01J 2219/00081* (2013.01)

(58) Field of Classification Search
CPC ...... C07D 251/60; C07D 251/62; B01J 19/24; B01J 3/04; B01J 10/00; B01J 4/00
USPC .................................................. 544/203, 201
See application file for complete search history.

(56) References Cited

U.S. PATENT DOCUMENTS

| | | |
|---|---|---|
| 2,979,308 A | 4/1961 | Putney |
| 3,271,116 A | 9/1966 | Hazelton |
| 3,278,420 A | 10/1966 | Jaeger |
| 5,486,339 A | 1/1996 | Bizzotto |
| 5,503,220 A | 4/1996 | Wood et al. |
| 6,815,545 B2 | 11/2004 | Bucka et al. |
| 2004/0054175 A1 | 3/2004 | Bucka et al. |

FOREIGN PATENT DOCUMENTS

| | | |
|---|---|---|
| FR | 1416096 A | 10/1965 |
| WO | 01/98281 A1 | 12/2001 |

OTHER PUBLICATIONS

International Search Report issued in connection with PCT/EP2015/054807.
International Preliminary Report on Patentability issued in connection with PCT/EP2015/054807.

*Primary Examiner* — Venkataraman Balasubramanian
(74) *Attorney, Agent, or Firm* — Akerman LLP

(57) ABSTRACT

Reactor for the synthesis of melamine from urea, in accordance with the high-pressure non-catalytic process, comprising: a vertical reactor body (1), at least one inlet (2) for the urea melt, a set of heating elements (3), and a central duct (7), said set of heating elements (3) being arranged inside said central duct.

12 Claims, 2 Drawing Sheets

HIGH-PRESSURE REACTOR FOR THE SYNTHESIS OF MELAMINE

This application is a national phase of PCT/EP2015/054807, filed Mar. 9, 2015, and claims priority to EP 14159283.2, filed Mar. 12, 2014, the entire contents of both of which are hereby incorporated by reference.

FIELD OF APPLICATION

The invention relates to a high-pressure reactor for the synthesis of melamine.

PRIOR ART

The processes for the synthesis of melamine from urea are commonly classified as low-pressure catalytic processes, typically below 1 MPa, and high-pressure non-catalytic catalytic processes, typically above 7 MPa. These processes are well-known in literature (see for example Ullmann's Encyclopedia of Industrial Chemistry, 6th ed., vol. 21, p. 205).

One of the known high-pressure synthesis processes, as described for example in U.S. Pat. No. 6,815,545, comprises essentially three steps: an endothermic reaction which converts urea into melamine inside a first reactor also termed primary reactor; a second step of carbon dioxide removal ($CO_2$) by introducing gaseous ammonia, and conversion of by-products into melamine, which is performed inside a second reactor called secondary reactor or stripping reactor; a third step wherein off-gases separated in the top part of the primary reactor and stripping reactor are extracted for washing or scrubbing with urea before they are recycled to the urea plant.

A plant designed to operate this process typically comprises a primary reactor, a secondary reactor and a scrubber, which are formed as separate cylindrical bodies. The urea melt is supplied to the primary reactor where the first reaction stage takes place, that is the endothermic conversion into melamine; the effluent of said primary reactor is then directed to the second reactor for stripping of the gases contained therein by means of gaseous ammonia. The liquid melamine is kept inside this secondary reactor for a certain residence time (aging of the melamine) in order to convert the by-products formed inside the primary reactor into melamine. The liquid effluent from the secondary reactor (melamine melt) may be sent to a subsequent further purification step.

The off-gas stream released inside the primary reactor and inside the secondary reactor mainly contains ammonia and $CO_2$ with small amounts of melamine. Said off-gas stream is washed with urea melt inside the scrubber. The urea melt is thus heated by said washing step, before being supplied to the primary reactor; the melamine-free off-gas stream at the scrubber outlet is exported and for example recycled for urea synthesis.

The pressure is generally between 70 and 250 bar (7-25 MPa) and typically about 100-120 bar (10-12 MPa).

U.S. Pat. No. 6,815,545 describes a primary reactor according to the prior art, which essentially comprises: a vertical cylindrical body; a central duct; a bundle of heating tubes arranged to form a ring around said central duct. The urea feed is introduced at the bottom of the central duct. Accordingly, a flow circulates in said prior art reactor by ascending the central duct and descending the annular region around the central duct where the heating tubes are mounted.

Said primary reactor design is widely used but has a number of drawbacks.

The tube bundle has an outer diameter which is almost equivalent to the diameter of the reactor body, i.e. of the entire apparatus. As the tube bundle must be removable for periodic maintenance, this design requires a fully open flange with a tubesheet which has substantially the same diameter as the reactor. The tubesheet is therefore thick, heavy and costly. It should be noted that the reactor operates at a high pressure (typically above 100 bar) and consequently a large flange and a large opening are expensive to realize and may create problems of tightness.

Another drawback is that the heating tube bundle is difficult to construct and hence costly; in particular, the heating tubes are bayonet (double-wall) tubes and require a double circular-rim tube plate, one of which has a large thickness.

A third drawback is that the urea inlet in the centre of the heating bundle must be disconnected and reconnected when maintenance is carried out. Said urea inlet, however, is difficult to access which means that disconnecting and reconnecting the urea inlet introduces a significant additional downtime; the difficult to access the respective flanged joint makes more difficult the making of a proper connection, which increases the risk of leakages from the seals.

SUMMARY OF THE INVENTION

The invention aims to overcome the drawbacks and problems mentioned above.

This purpose is achieved with a reactor and a process for the synthesis of melamine from urea using the high-pressure non-catalytic process, according to the accompanying claims.

The reactor comprises a vertical body, at least one inlet for the urea melt, a set of heating elements, and a central duct, and is characterized in that said central duct delimits an inner reaction zone and a peripheral reaction zone, and said set of heating elements is arranged inside said central duct.

Said central duct is advantageously delimited by a shell, preferably cylindrical, which surrounds the set of heating elements. This shell may be defined as being a low-pressure shell situated inside the reactor. The outer shell of the reactor may be defined as being a high-pressure shell, since it withstands the high pressure of the process.

The central duct delimits an inner reaction zone and a peripheral reaction zone which communicate with each other and inside which a circulation flow is formed. The peripheral zone has the form of a circular crown in a cross section, and may be externally delimited by the shell of the reactor itself (high-pressure shell) or possibly by another shell inside the shell of the reactor.

Advantageously, according to the invention, no heating element is placed in the peripheral zone around the central duct; hence this zone does not have any heating elements.

According to the invention, the heating elements are arranged in the centre of the reactor, i.e. in the inner zone, rather than in the peripheral zone around the duct. Preferably, the set of heating elements is a bundle of tubes which are connected to a tube plate at the bottom of the reactor and supplied with a suitable thermal fluid.

In a preferred embodiment, the reactor comprises a distributor for the urea feed, which is connected to said urea melt inlet and is configured to introduce urea into said peripheral reaction zone. More advantageously, said distributor is configured to introduce urea in a substantially uniform manner and with axially symmetry into said peripheral zone.

In a preferred embodiment, said distributor is a toroidal body with a plurality of urea distribution holes distributed along its circumference; the distribution holes are preferably directed so as to favour mixing of the urea melt with a stream exiting the inner reaction zone. More preferably said distributor is arranged around the base or around a lower portion of the central duct.

In a preferred embodiment, a lower end of the central duct is distanced from a base of the set of heating elements, thus defining a passage for the recirculation of liquid. More preferably, said central duct extends, inside the reactor, up to a height lower than the height of the heating elements.

As a result of the configuration described a descending flow is established inside the central duct in the presence of the heating elements, and an ascending recirculating flow is established in the surrounding annular zone where there are no heating elements. Hence the flow is descending in the heated reaction zone, as in the reactors of the prior art, which is an advantage because the process conditions which are familiar to persons skilled in the art are retained. At the same time, the invention provides the constructional advantages arising from the location of the heating tubes in the central part of the reactor.

The mixing of the two fluids is ensured by the axial symmetry inside the annular cavity.

A deflector in the form of a circular crown is preferably installed at the top end of the peripheral reaction zone. Said deflector prevents turbulence on the free surface of the fluid inside the reactor and direct the flow into the inner zone containing the heating bundle. In certain preferred embodiments the header for the liquid melamine may be associated with said deflector.

The invention also relates to a process for the high-pressure synthesis of melamine from urea according to the claims.

The process comprises a primary reaction stage in which a stream of urea is converted into melamine with an endothermic reaction, inside a vertical reactor; said primary reaction stage is performed by establishing a circulatory flow in a liquid mass comprising melamine and urea; said flow comprises a descending flow in a substantially column-like region in the centre of said reactor, directly heated by the presence of heating elements, and a non-heated ascending flow in a peripheral region around said column, without heating elements, where the urea feed is introduced. The term of non-heated means that no heating means, such as heating tubes, are provided in the peripheral region of the ascending flow.

The invention has the following advantages. The set of heating elements is less complex, more compact, easier to manufacture and therefore less costly than the conventional reactors, owing to the location in the centre of the reactor. In fact, the heating elements are arranged in a substantially cylindrical zone in the centre of the reactor, instead of in an annular zone with the same outer diameter of the reactor itself.

With reference, for example, to heating elements in the form of tubes, the tubesheet has a smaller diameter and a smaller thickness, and the reactor body has a lower cost because the flange coupling with the tubesheet is partially open rather than fully open. Owing to the proposed configuration, the periodic operation of disassembly of the heating bundle is simplified since it is no longer required to remove and restore the connections of the urea melt feed line. Consequently the plant downtimes are reduced. Design and manufacturing of large-size reactors is less challenging due to the smaller and simpler heating bundle.

In some embodiments, a reactor according to the invention may also incorporate a second reaction chamber, also called secondary section, for stripping the liquid melamine with ammonia, and/or a section for scrubbing the gases.

The invention will be further elucidated with the help of the following description of a preferred embodiment, described by way of a non-limiting example.

DETAILED DESCRIPTION

Figure 1:
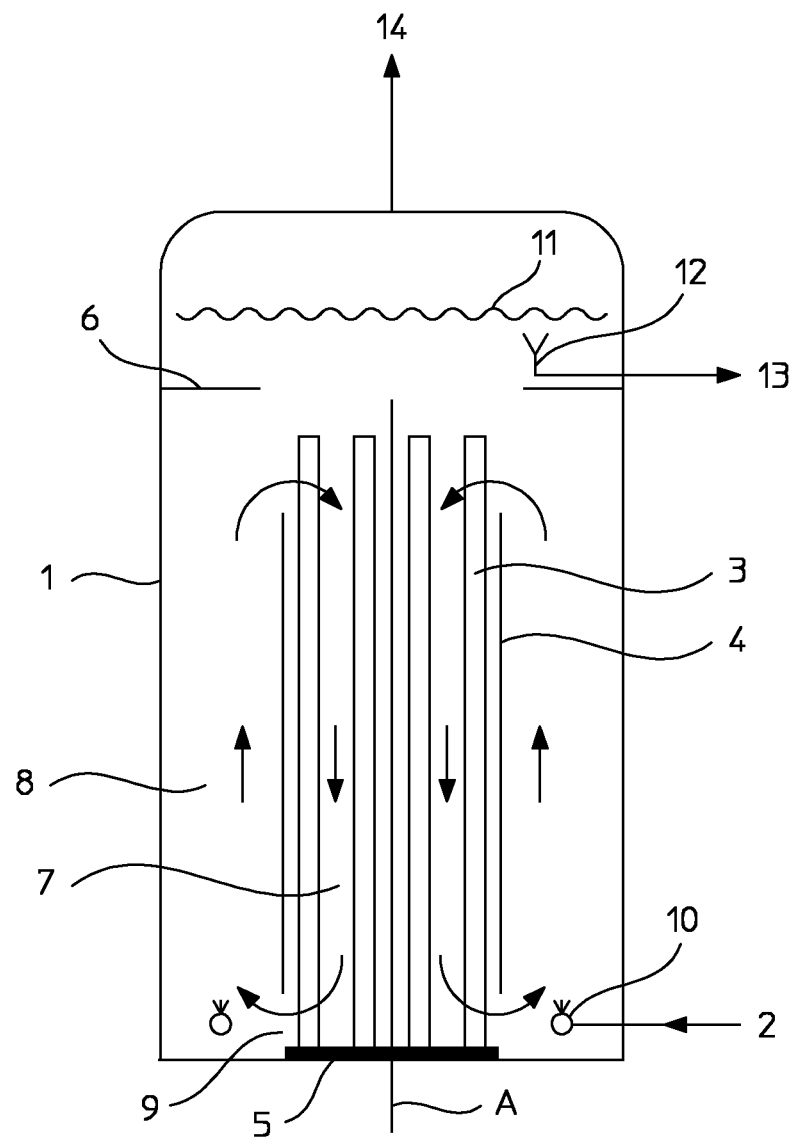
FIG. 1 is a schematic cross-section of a primary reactor for the high-pressure synthesis of melamine, according to a preferred embodiment of the invention.

FIG. 1 shows an example of a reactor which comprises a vertical body 1, an inlet 2 for a urea melt, and a bundle of heating tubes 3 inside a central duct 7, which is delimited by a cylindrical shell 4.

The tubes 3 are fixed to a tubesheet 5 which is located at the bottom of the reactor.

The body 1 and the shell 4 are substantially axially symmetrical; preferably both the body 1 and the shell 4 are cylindrical.

Said shell 4 may be termed a low-pressure inner shell. It remains immersed inside the liquid melamine during operation and is not subject to a substantial difference in pressure.

The top of shell 4 is advantageously lower than the top of the tubes 3, as shown.

The shell 4 also delimits a substantially annular region 8 outside the duct 7. Said region 8 forms a peripheral reaction zone around the central duct 7. In the example of FIG. 1 said region 8 is delimited between the shell 4 and the cylindrical body 1; in other embodiments, however, the outer peripheral bound of said region 8 may be delimited by another low-pressure shell inside the body 1.

The bottom edge of the shell 4 is spaced from the tube plate 5, leaving a passage 9 for recirculation of the liquid.

The urea feed line 2 is connected to a toroidal distributor 10 provided with a plurality of urea distribution holes along its circumference. Thus configured, the distributor 10 introduces urea in a uniform manner into the annular region 8.

Advantageously said urea distributor 10 is at the base of the duct 7, as shown in FIG. 1, in the same region of said recirculation passage 9. In some variants (not shown) the toroidal body of said distributor 10 may be positioned on the outer diameter of the reactor body 1 or outside the reactor itself, so as to be accessible externally.

A diaphragm 6 is advantageously provided at the top of the annular region 8.

Under normal operating conditions, the reactor is almost completely full of liquid, reaching the level 11 as indicated in the figures. The flow line 13 indicates the crude melamine exiting via a suitable header 12. The flow line 14 indicates the gases mainly containing ammonia and $CO_2$ (off-gases) which are extracted from the top of the reactor.

The arrows in FIG. 1 indicate the axially symmetrical recirculating flow which is established inside the reactor. A descending flow is generated inside the central duct 7, said flow entering the base of the annular section 8 via the passage 9, and mixing with the urea feed. An ascending flow is established inside the annular section 8, assisted by the formation of bubbles in the liquid phase. Part of the liquid mass which emerges from the top of the annular section 8, also as a result of the deflector 6, recirculates with a descending flow back into the duct 7 via the open top end of the shell 4.

The conversion of urea into melamine takes place in the zones 7 and 8 in accordance with the known reaction: 6 urea melamine→6 $NH_3$+3 $CO_2$ (off-gas).

From FIG. 1 it is possible to better appreciate a number of advantages of the invention and in particular: the diameter of the flange 5 is relatively small, owing to the central arrangement of the tube bundle 3; the circulating flow inside the reactor descends inside the region directly in contact with the heating elements (i.e. inside the duct 7) and ascends inside the annular portion 8.

The reactor has a substantially radial symmetry relative to the axis A. In particular, the duct 7, the annular chamber 8 and the distributor 10 have a substantial radial symmetry relative to said axis A. Therefore, the reactor may be defined axially symmetrical and the flow of the liquid is substantially axially symmetrical.

FIG. 1 shows an embodiment in which the melamine 13 is drawn off at a specific point via the header 12.

Figure 2:
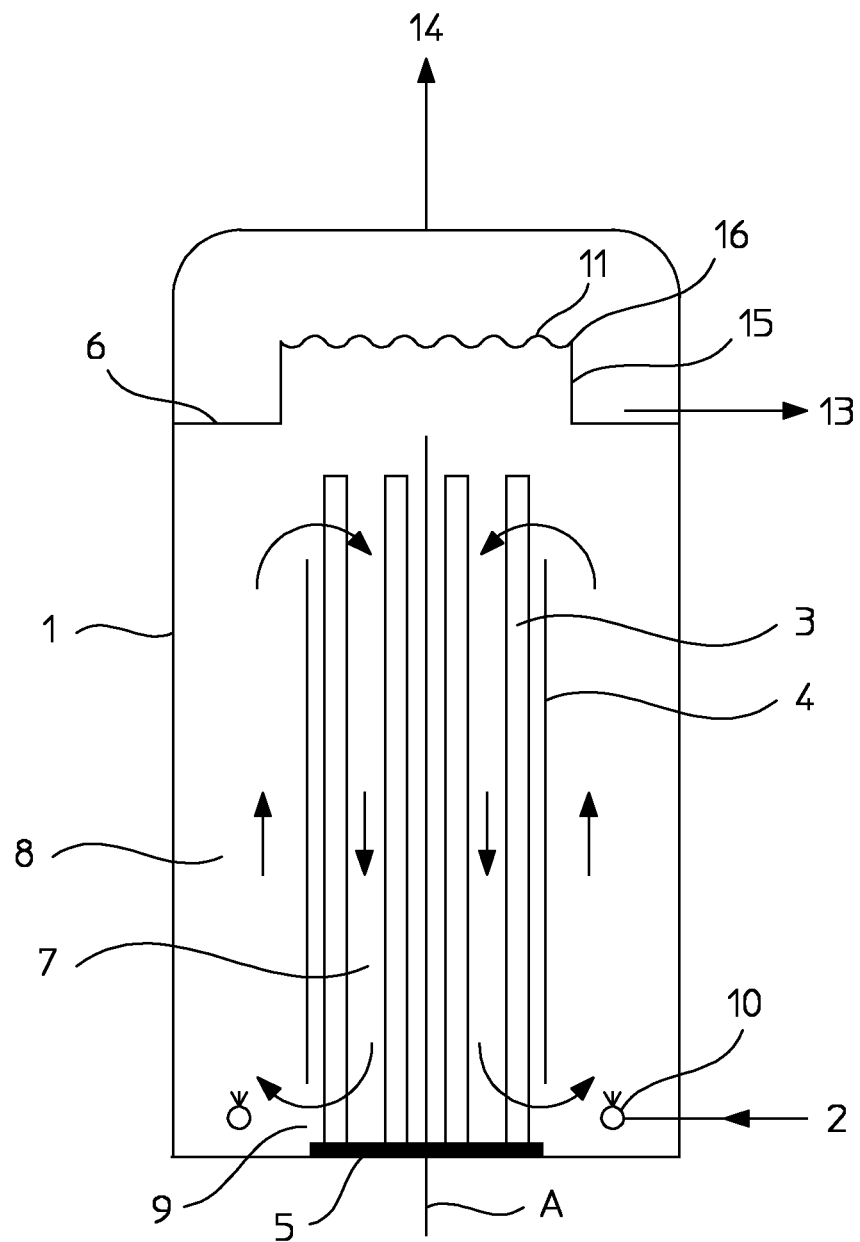
FIG. 2 shows a variant of the reactor shown in FIG. 1, according to another embodiment of the invention.

In the variant according to FIG. 2, the header for collecting the crude melamine is advantageously formed above the deflector 6, thus allowing uniform collection of the melamine product along the whole circumference of the reactor.

More preferably, a reactor of this embodiment comprises a melamine header 15 having a top peripheral edge 16 positioned above said deflector 6. The melamine emerges through said header 15 and, once reached the edge 16, it flows out onto the deflector 6 which acts as melamine collector. In this embodiment, the collection of melamine takes place in a distributed and substantially axially symmetrical manner along a circumference formed, in the example, by the edge 16. The advantage of an improved symmetry of the flows is thus obtained.

The invention claimed is:

1. A reactor for the synthesis of melamine from urea, according to a high-pressure non-catalytic process, comprising:
a vertical reactor body, at least one inlet for the urea melt, a set of heating elements, and a central duct, wherein: said central duct delimits an inner reaction zone inside said duct, and a peripheral reaction zone around said duct, and said set of heating elements is arranged in the inner reaction zone inside said central duct.

2. The reactor according to claim 1, characterized by comprising no heating element inside said peripheral reaction zone.

3. The reactor according to claim 1, wherein said inlet for the urea melt is connected to a distributor configured to introduce urea into said peripheral reaction zone.

4. The reactor according to claim 3, said distributor being extended around the central duct and comprising urea delivery means which are arranged to introduce urea in a substantially uniform manner and with axial symmetry into said peripheral reaction zone.

5. The reactor according to claim 4, wherein said distributor has a substantially toroidal form.

6. The reactor according to claim 1, wherein a lower end of said central duct is distanced from a base of the set of heating elements, thus defining a liquid recirculation passage between the inner reaction zone and the surrounding peripheral reaction zone.

7. The reactor according to claim 1, wherein said central duct extends, inside the reactor, up to a height lower than the height of the heating elements.

8. The reactor according to claim 1, wherein said central duct is delimited by a substantially cylindrical shell.

9. The reactor according to claim 1, wherein said set of heating elements is a bundle of tubes connected to a tube sheet at the bottom of the reactor.

10. The reactor according to claim 1, wherein the urea inlet is at the base of the peripheral region and is arranged to feed urea with an upward flow, and a recirculation passage is provided at the base of the central duct, in such a way that the reactor operates with an ascending flow in the peripheral reaction zone and a descending flow in the central duct where the heating elements are installed.

11. The reactor according to claim 1, comprising a deflector which is in the form of circular crown and is located at the top of said peripheral reaction zone, said deflector being preferably flat or frusto-conical.

12. The reactor according to claim 11, comprising a header for collecting the melamine, said header being associated with said deflector and configured to collect melamine in a distributed manner along a circumference.

* * * * *